(12) United States Patent
Di Girolamo et al.

(10) Patent No.: US 6,500,999 B2
(45) Date of Patent: Dec. 31, 2002

(54) PROCESS FOR THE PRODUCTION OF HYDROCARBONS WITH A HIGH OCTANE NUMBER BY MEANS OF THE SELECTIVE DIMERIZATION OF ISOBUTENE WITH ACID CATALYSTS

(75) Inventors: Mario Di Girolamo, Milan (IT); Mario Marchionna, Milan (IT); Lorenzo Tagliabue, Milan (IT)

(73) Assignee: Snamprogetti S.p.A., San Donato Milanese (IT)

( * ) Notice: Subject to any disclaimer, the term of this patent is extended or adjusted under 35 U.S.C. 154(b) by 0 days.

(21) Appl. No.: 09/761,781

(22) Filed: Jan. 18, 2001

(65) Prior Publication Data

US 2002/0002316 A1 Jan. 3, 2002

(30) Foreign Application Priority Data

May 26, 2000 (IT) .......................................... MI00A1166

(51) Int. Cl.[7] .............................. C07C 2/04; C07C 2/02; C07C 2/24

(52) U.S. Cl. ...................... 585/510; 585/502; 585/514; 585/515; 585/526; 585/524; 585/533

(58) Field of Search ................................. 585/510, 502, 585/514, 515, 526, 524, 533

(56) References Cited

U.S. PATENT DOCUMENTS 6,011,191 A * 1/2000 Di Girolamo et al. ...... 585/514

* cited by examiner

Primary Examiner—Thuan D. Dang
(74) Attorney, Agent, or Firm—Oblon, Spivak, McClelland, Maier & Neustadt, P.C.

(57) ABSTRACT

A process is described for the production of hydrocarbons with a high octane number starting from hydrocarbon cuts containing isobutene by means of selective dimerization with acid catalysts, characterized in that the dimerization reaction is carried out in a tubular reactor using a feeding containing isobutene in quantities of less than 20% by weight and with a molar ratio linear olefins/isobutene greater than 3, preferably operating at a reaction temperature ranging from 30 to 120° C., at a pressure of less than 5 MPa and at feeding space velocities of less than 60 $h^{-1}$.

13 Claims, 1 Drawing Sheet

PROCESS FOR THE PRODUCTION OF HYDROCARBONS WITH A HIGH OCTANE NUMBER BY MEANS OF THE SELECTIVE DIMERIZATION OF ISOBUTENE WITH ACID CATALYSTS

BACKGROUND OF THE INVENTION

Field of the Invention

The present invention relates to a process for the production of hydrocarbons with a high octane number, obtained by the selective dimerization reaction, in a tubular reactor, of the isobutene contained in hydrocarbon cuts, characterized by a low isobutene content and a high linear olefin/isobutene ratio (>3), which favours the production of higher selectivities on the part of the catalyst. The mixture obtained can then be hydrogenated with the conventional methods to obtain a product with further improved octane characteristics.

Description of the Background

At present, refineries throughout the whole world are producing "Environmental Low Impact Gasolines" (characterized by a reduced content of aromatics, olefins, sulfur and a lower volatility), obviously with the aim of minimizing the effect of their production on the functioning of the refinery itself.

MTBE and alkylated products are the most suitable compounds for satisfying future refinery demands; however, at the moment, the use of MTBE is extremely risky and alkylated products are not easily available.

The ban of MTBE from gasolines in California and the continual attacks to which it is subjected, owing to its presumed toxicity, have in fact jeopardized its use (and also that of other alkyl ethers) in future reformulated gasolines. The removal of this ether will create considerable problems in refineries as MTBE, in addition to its high-octane function, also has a diluting action of the products which are most harmful for the environment (sulfur, aromatics, benzene, etc.,). The alkylated product is undoubtedly the ideal compound for reformulated gasolines, as it satisfies all the requisites provided for by future environmental regulations owing to the combination of a high octane number with a low volatility and a complete absence of olefins and aromatics.

Another positive aspect of alkylation is its capacity to activate isoparaffinic hydrocarbons, such as isobutane, for example, which binds itself, by reaction in liquid phase catalyzed by strong acids, with olefins (propylene, butenes, pentenes and relative mixtures) creating saturated $C_7$–$C_9$ hydrocarbons with a high octane number.

Quantities of alkylated product, however, greater than those at present available, would require the construction of large alkylation units as at present, owing to its scarcity, it is not a commodity which is widely available on the market but is a gasoline component used exclusively in refineries where it is produced.

This represents a serious limitation in the use of alkylated products on a wide scale, as the construction of new units is limited by the incompatibility of the catalysts used in traditional processes (hydrofluoric acid and sulfuric acid) with the new environmental regulations; the process with hydrofluoric acid owing to the toxicity of this acid, especially in populated areas, and the process with sulfuric acid owing to the large production of acid mud as well as the considerable corrosive capacity of the catalyst.

Alternative processes are being developed with solid acid catalysts but their commercial applicability has still to be demonstrated.

To solve these problems, it will therefore be necessary to resort more and more to the use of purely hydrocarbon products, such as those obtained by the selective dimerization of $C_3$ and $C_4$ olefins, which owing to their octane characteristics (high Research Octane Number (RON) and Motor Octane Number (MON)) and also their boiling point (limited volatility but low end point) are included in the range of compositions which are extremely interesting for obtaining gasolines which are more compatible with present-day environmental demands.

The oligomerization process (often incorrectly called polymerization) was widely used in refining in the '30s' and '40s' to convert low-boiling $C_3$–$C_4$ olefins into the so-called "polymer" gasoline. Typical olefins which are oligomerized are mainly propylene, which gives dimers ($C_6$) or slightly higher oligomers depending on the process used, and isobutene which mainly gives dimers ($C_8$) but always accompanied by large quantities of higher oligomers ($C_{12}$+).

This process leads to the production of a gasoline with a high octane number (RON about 97) but with a high sensitivity due to the purely olefinic characteristic of the product (for more specific details on the process see: J. H. Gary, G. E. Handwerk, "Petroleum Refining: Technology and Economics", $3^{rd}$ Ed., M. Dekker, New York, (1994), 250). The olefinicity of the product obviously limits the process as the hydrogenation of these mixtures always causes a considerable reduction in the octane characteristics of the product, which thus loses its appeal.

If we limit our attention to the oligomerization of isobutene, it is known that this reaction can be carried out batchwise, in semi-continuous and in continuous, both in gas-solid phase and in liquid phase, generally at temperatures ranging from 50 to 300° C. and a atmospheric pressure or at such pressures as to keep the reagents in liquid phase, if considered necessary.

The dimerization of isobutene is generally carried out with acid catalysts such as phosphoric acid, generally supported on a solid (for example kieselguhr), cationic exchange acid resins, liquid acids such as $H_2SO_4$, sulfonic acid derivatives, silico-aluminas, mixed oxides, zeolites, fluorinated or chlorinated aluminas, etc.

The main problem of dimerization, which has hindered its industrial development, is the difficulty in controlling the reaction rate; the considerable activity of all these catalytic species, together with the difficulty in controlling the temperature in the reactor, in fact, makes it extremely problematical to limit the addition reactions of isobutene to the ever lengthening chains and, consequently to produce a high quality product characterized by a high selectivity to dimers.

In the dimerization reaction, there is, in fact, the formation of excessive percentages of heavy oligomers such as trimers (selectivity of 15–60%) and tetramers (selectivity of 2–10%) of isobutene. Tetramers are completely excluded from the gasoline fraction as they are too high-boiling and therefore represent a net loss in yield to gasoline; as far as trimers are concerned (or their hydrogentated derivatives), it is preferable to greatly reduce their concentration, as their boiling point (170–180° C.) is on the limit of future specifications on the final point of reformulated gasolines.

From what is specified above, it is evident that there is great interest in obtaining a new dimerization process of isobutene which allows the synthesis of a higher quality product, by reaching greater selectivities.

SUMMARY OF THE INVENTION

It has now been surprisingly found that high selectivities can be obtained by using hydrocarbon charges which are particularly rich in linear olefins and by carrying out the dimerization reaction of isobutene in a tubular reactor capable of removing the heat as it is generated. Operating as such, it is possible to obtain the production of an oligomer fraction particularly rich in dimers (>80% weight).

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
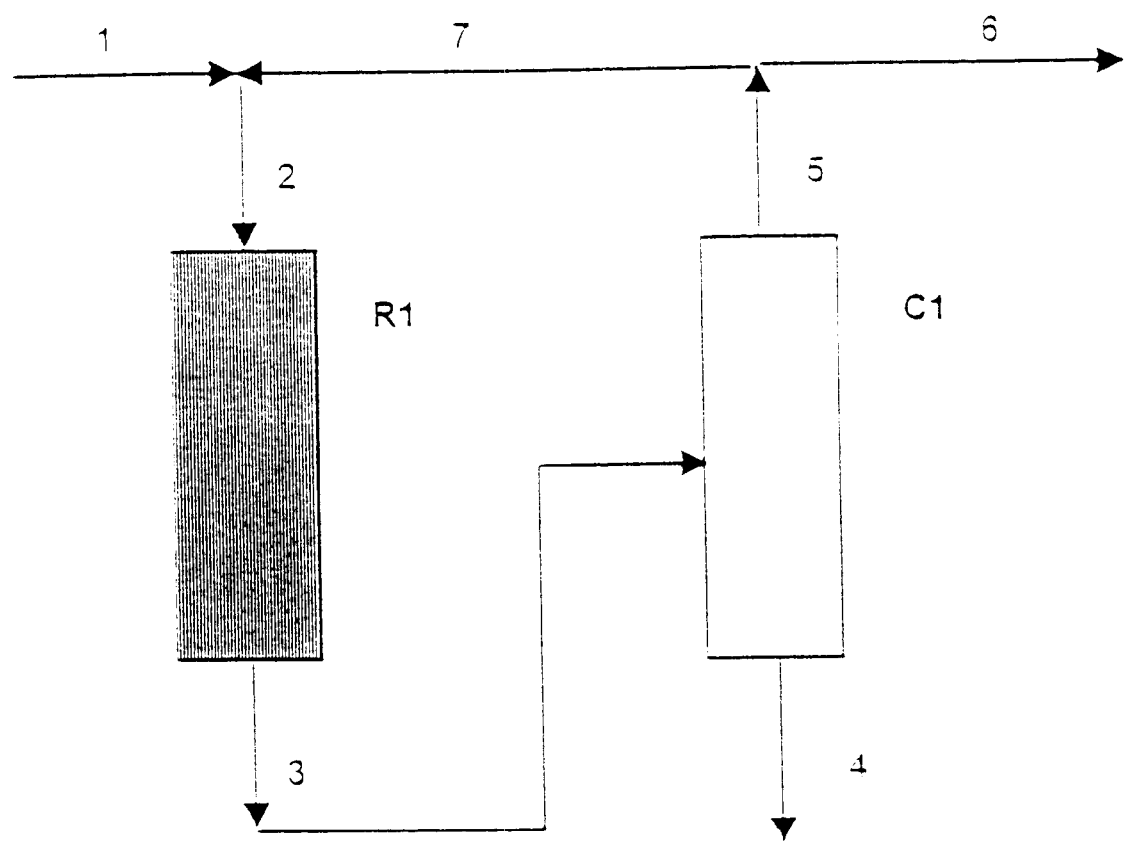
FIG. 1 is a flow scheme of the oligomerization process of the present invention in which isobutene is converted to $C_8$ hydrocarbon product in enhanced selectivity.

The use of a tubular reactor is fundamental for obtaining high selectivities in that it allows an optimum temperature control in the reactor, removing the heat as it is generated along the catalytic bed.

In this way the temperature peak is situated in the initial part of the reactor (greater reaction rate) where the concentration of isobutene is higher, whereas in the remaining part of the reactor, where the concentration of $C_8$ olefins, which can be transformed to heavy oligomers, is higher, the temperature is lower and tends to become uniform with that of the cooling fluid.

Operating under these conditions, the dimerization of isobutene or co-dimerization of isobutene/n-butenes, is therefore favored with respect to the oligomerization and the activating of oligomerization-polymerization reactions of linear butenes which are favored at high temperatures, is avoided.

Alternative reactor configurations, such as for example, the adiabatic reactor, cannot be used for this reaction as higher temperatures are reached at the outlet of the catalytic bed (where the concentration of isobutene is minimum) and consequently oligomerization reactions are developed with a considerable drop in the selectivity.

The reaction product is then preferably hydrogenated to give a completely saturated end-product with a high octane number and low sensitivity. The hydrogenation can be carried out with conventional methods as described for example in F. Asinger, "Mono-olefins: Chemistry and Technology", Pergamon Press, Oxford, page 455.

As an example, Table 1 indicates the octane number and relative boiling points of some of the products obtained by means of the process object of the present invention.

TABLE 1

| PRODUCT | RON | MON | b.p. (° C.) |
|---|---|---|---|
| Diisobutylenes | 100 | 89 | 100–105 |
| Iso-octane | 100 | 100 | 99 |
| Tri-isobutylenes | 100 | 89 | 175–185 |
| Hydrogenated tri-isobutylenes | 101 | 102 | 170–180 |

The process, object of the present invention, for the production of hydrocarbons with a high octane number by means of selective dimerization with acid catalysts, is characterized in that the dimerization reaction is carried out in a tubular reactor using a feeding containing isobutene in a quantity of less than 20% by weight and with a molar ratio linear olefins/isobutene greater than 3.

The content of isobutene and molar ratio linear olefins/isobutene can be obtained by mixing the fresh charge with at least a part of the hydrocarbon stream obtained after separation from the product.

The use of a tubular reactor allows the heat to be removed as soon as it is formed and ensures optimum control of the reaction temperature, thus avoiding self-condensation reactions of the linear olefins.

The latter, as well as moderating the activity of the resin, are partially transformed by means of the co-dimerization reaction with isobutene to hydrocarbon product without influencing, however, the octane value of the mixture.

An enriching treatment of the internal linear olefins is therefore also possible, by means of pre-isomerization, as this favors the overall octane number of the mixture.

The process claimed herein can be mainly applied to cuts containing isobutane, n-butane and n-butenes.

Although there is a wide variety of sources for supplying these streams, the most common ones are those deriving from FCC units and streams coming from Steam-Crackers, dehydrogenation processes of isoparaffins or isobutene streams deriving from the dehydration of tert and/or isobutanol.

When Steam-Cracking streams contain diolefins, in addition to the desired mono-olefins, they should be eliminated by means of typical removal treatment (for example extractions or selective hydrogenations).

Table 2 indicates the average compositions of typical $C_4$ hydrocarbon fractions coming from different sources (FCC, Steam Cracking, dehydrogenation of isobutane, dehydration processes).

TABLE 2

|  | Steam Cracking | DEHYDROGEN. | FCC | DEHYDRATION |
|---|---|---|---|---|
| Isobutene | 30–50 | 45–55 | 10–25 | >99 |
| n-butenes | 30–60 |  | 25–50 | <1 |
| saturated $C_4$ | 4–10 | 45–55 | 30–60 | <1 |

On examining the table, it can be seen that in the case of streams coming from the dehydrogenation of isobutane or from dehydration, there are no significant concentrations of linear butenes in the charge, capable of influencing the catalyst, and it is therefore not possible to control the selectivity of the dimerization without an external addition of charges containing linear olefins.

On the contrary, for charges from FCC, Steam-Cracking or also from the dehydrogenation of isobutane/n-butane mixtures, it is possible to produce a hydrocarbon stream rich in dimers (selectivity >80%) by suitably modifying the composition of the charge by recycling at least part of the non-reacted linear olefins (together with the butanes) in such a quantity as to give the correct concentrations of linear butenes and isobutene at the reactor inlet.

The following values are therefore recommended depending on the type of charge used:

for a feeding containing quantities of saturated hydrocarbons higher than 15% by weight, for example in the case of charges coming from FCC units and having a high content of butanes (normal and iso), the concentration of isobutene should be preferably kept equal to or less than 10% by weight;

for a feeding containing quantities of saturated hydrocarbons lower than 15% by weight, for example in the case of charges coming from Steam-Cracking units and having a high content of linear olefins in the charge, the concentration of isobutene should be preferably kept equal to or less than 20% by weight.

In the feeding, the linear olefins preferably contain from 3 to 7 carbon atoms, preferably from 4 to 5 carbon atoms.

In the case of charges containing $C_3$ hydrocarbons, their concentration will be lower than that of the isobutene in the charge; when the streams used also contain $C_5$ olefins, linear or branched, these can be recycled to the reactor together with the linear butenes as they also contribute to improving the selectivity. Part of these olefins can also be co-dimerized with isobutene as in the case of n-butenes.

A simplified process scheme is shown in the FIGURE to provide a clearer illustration of the present invention.

The stream (1) containing isobutene, for example coming from Steam-Cracking or FCC units from the dehydrogenation of isobutane/n-butane mixtures, is sent together with a recycled stream (7) (consisting of linear olefins, n-butane, isobutane and non-reacted isobutene) through line 2 to a reactor (Rl) in which the isobutene is selectively converted to dimers.

The effluent (3) from the reactor is sent to a separation column (C1) where a stream (5) essentially containing non-converted isobutene, linear olefins and $C_4$ saturated products (n-butane and isobutane) is removed at the head whereas a stream (4) consisting of dimers and higher oligomers is removed from the bottom.

The stream (5) is then separated and a part is sent to the dimerization reactor (7) whereas the other part (6) is used in the subsequent conversion operations (alkylation, hydrogenation, etc.). The relative ratio between the streams (6) and (7) is in relation to the isobutene content in the charge and the derivation of the charge itself. Macroreticulated sulfonated resins, such as for example Amberlyst 15 and Amberlyst 35 produced by Rohm & Haas, are preferred as catalysts for this process. The characteristics of these resins, generally copolymers of styrene and divinylbenzene, are widely described in literature (see for example A. Mitschker, R. Wagner, P. M. Lange, "Heterogeneous Catalysis and Fine Chemicals", M. Guisnet ed., Elsevier, Amsterdam, (1988), 61).

A wide range of operating conditions can be used for producing hydrocarbons with a high octane number from isobutene in the desired selectivities by means of the object of the present invention. It is possible to operate in vapor phase or in liquid-vapor phase but operating conditions in liquid phase are preferred.

The process, object of the present invention, can operate both under batch and continuous conditions. It should be reminded, however, that the latter are much more advantageous in industrial practice.

The range of process conditions, operating in liquid phase, includes a wide variety of operating conditions which are described hereunder.

The pressure is preferably super-atmospheric to keep the reagents in liquid phase, generally below 5 MPa, more preferably between 0.2–2.5 MPa. The reaction temperature preferably ranges from 30 to 120° C.

The feeding space velocities of the hydrocarbon streams should be preferably less than 60 $h^{-1}$, more preferably ranging from 1 to 40 $h^{-1}$.

The pre-selected reactor configuration is a fixed bed tubular reactor which allows optimum temperature control and therefore favors dimerization with respect to oligomerization. This reactor can be fed downwards with a stream of reagents (down-flow) or upwards (up-flow), with the stream of cooling fluid in equi or counter-current with respect to the reagents and catalyst, which can be situated either inside or outside the tubes. A large quantity of substances can be used for removing the reaction heat but water and also the hydrocarbon charge itself are preferred.

Some examples are provided for a better illustration of the invention but should not be considered as limiting its scope in any way.

EXAMPLE 1

This example illustrates the use of the process of the present invention in a tubular reactor. The reactor used consists of a stainless steel jacketed tube (internal diameter of 1.4 cm) into which the acid resin is charged. The reaction heat is removed by the circulation in counter-current of water at a certain temperature. Operating in this way a thermal profile can be obtained which is analogous to that of an industrial tubular reactor with the temperature peak positioned in the initial part of the reactor. It is also possible to observe the temperature profile in the reactor by means of a mobile thermocouple.

A hydrocarbon stream having the following composition:

| | |
|---|---|
| Isobutene | 11.0% by weight |
| n-Butenes | 77.9% by weight |
| Butanes (iso + n) | 11.1% by weight | is sent to the reactor, into which 20 cc of commercial sulfonated macroporous resin of the type Amberlyst 35, have been charged, at a temperature of 45° C., a constant pressure of 1.5 MPa (sufficient for keeping the reagents liquid) and an hourly space velocity of 10 (reagent volume/catalyst volume).

The reaction heat developed is removed by water circulation at 45° C. in the reactor jacket in order to have a maximum temperature of 80° C. in the reactor.

The results obtained are indicated in Table 3:

TABLE 3

| | CONVERSION % | | SELECTIVITY % | | |
|---|---|---|---|---|---|
| | Isobutene | n-butenes | $C_8$ | $C_{12}$ | $C_{16}+$ |
| EXAMPLE 1 | 85 | 2 | 83.2 | 15.6 | 1.2 |
| EXAMPLE 2 | 90 | 5 | 57.3 | 36.1 | 6.6 |
| EXAMPLE 3 | 92 | — | 36.1 | 55.0 | 8.9 |

EXAMPLE 2 (Comparative)

This example demonstrates that if the reaction is carried out with a concentration of isobutene which is too high, it is not possible to control the oligomerization rate, with the formation of high quantities of heavy oligomers.

This test was carried out with the same equipment and under the same operating conditions described in example 1.

In this example a hydrocarbon stream was used, coming from a Steam-cracker and having the following composition:

|   |   |
|---|---|
| Isobutene | 44.1% by weight |
| n-Butenes | 51.8% by weight |
| Butanes (iso + n) | 4.1% by weight |

With respect to the previous example, the larger quantity of isobutene makes it much more difficult to control the temperature inside the reactor where the temperature of the peak reaches 1000° C., in spite of the use of cooling water at 30° C.

Table 3 indicates the results obtained.

EXAMPLE 3 (Comparative)

This example demonstrates that if the reaction is carried out without linear olefins, it is not possible to control the oligomerization reaction with $C_{12}$ trimers which become the main product, as can be seen from Table 3.

This test was also carried out with the same equipment and operating conditions described in example 1, except for the use of thermostat-regulation water at 15° C., which allowed the peak to be maintained at 90° C.

In this example a hydrocarbon stream was used, containing 50% by weight of isobutene, of the same type as that obtained by the dehydrogenation of isobutane:

|   |   |
|---|---|
| Isobutene | 49.6% by weight |
| n-Butenes | 0.4% by weight |
| Butanes (iso + n) | 50.0% by weight. |

What is claimed is:

1. A process for the production of hydrocarbons having a high octane number, comprising:
   conducting oligomerization of unsaturated components in a hydrocarbon feed material consisting essentially of isobutene, linear olefins and light saturated hydrocarbon compounds in the presence of an acid catalyst in a tubular reactor, wherein the content of isobutene in the feed material is less than 20 wt % and wherein the mole ratio of linear olefin/isobutene is greater than 3, thereby achieving greater selectivity to dimerized $C_8$ hydrocarbon product.

2. The process according to claim 1, wherein, the content of isobutene and the molar ratio of linear olefins/isobutene in a charge of hydrocarbon feed material are established by mixing the charge of hydrocarbon feed material with at least a portion of the hydrocarbon product obtained from the oligomerization reaction.

3. The process according to claim 1, wherein, when the hydrocarbon feed material contains quantities of saturated hydrocarbons greater than 15% by weight of the feed material, the concentration of isobutene must be kept equal to or less than 10% by weight of the feed material.

4. The process according to claim 1, wherein, when the hydrocarbon feed material contains quantities of saturated hydrocarbons less than 15% by weight, the concentration of isobutene must be kept less than 20% by weight.

5. The process according to claim 1, wherein the linear olefins in the hydrocarbon feed material contain from 3 to 7 carbon atoms.

6. The process according to claim 5, wherein the linear olefins contain from 4 to 5 carbon atoms.

7. The process according to claim 5, wherein the concentration of $C_3$ olefins is lower than that of isobutene.

8. The process according to claim 1, wherein the oligomerization reaction is conducted at a reaction temperature ranging from 30 to 120° C, at a pressure of less than 5 MPa and at a feed space velocity of less than 60 $h^{-1}$.

9. The process according to claim 6, wherein the feed space velocity ranges from 1 to 40 $h^{-1}$.

10. The process according to claim 1, wherein the tubular reactor is cooled with water as a cooling fluid.

11. The process according to claim 1, wherein the charge of hydrocarbon feed to the tubular reactor itself cools the reactor.

12. The process according to claim 1, wherein the acid catalyst is phosphoric acid supported on a solid carrier, a cationic acid exchange resin, a liquid acid, a sulfonic acid derivative, a silico-alumina, a mixed oxide, a zeolite or a fluorinated or chlorinated alumina.

13. A process for the production of hydrocarbons having a high octane number, comprising:
   conducting oligomerization of unsaturated components in a hydrocarbon feed material consisting essentially of isobutene, linear olefins and butanes in the presence of an acid catalyst in a tubular reactor, wherein the content of isobutane in the feed material is less than 20 wt % and wherein the mole ratio of linear olefin/isobutene is greater than 3, thereby achieving greater selectivity to dimerized $C_8$ hydrocarbon product.

\* \* \* \* \*

UNITED STATES PATENT AND TRADEMARK OFFICE
CERTIFICATE OF CORRECTION

PATENT NO. : 6,500,999 B2
DATED : December 31, 2002
INVENTOR(S) : Di Girolamo et al.

It is certified that error appears in the above-identified patent and that said Letters Patent is hereby corrected as shown below:

<u>Title page,</u>
Item [30], Foreign Application Priority Data, should read:

-- [30]   Foreign Application Priority Data

May 26, 2000   (IT) ............................. MI2000A001166 --

Signed and Sealed this

Twentieth Day of May, 2003

JAMES E. ROGAN
*Director of the United States Patent and Trademark Office*